United States Patent [19]
Herweck et al.

[11] Patent Number: 5,370,681
[45] Date of Patent: Dec. 6, 1994

[54] POLYUMENAL IMPLANTABLE ORGAN

[75] Inventors: Steve A. Herweck, Nashua; Theodore Karwoski, Hollis; Paul Martakos, Pelham, all of N.H.

[73] Assignee: Atrium Medical Corporation, Hudson, N.H.

[21] Appl. No.: 29,990

[22] Filed: Mar. 12, 1993

Related U.S. Application Data

[63] Continuation of Ser. No. 760,717, Sep. 16, 1991, abandoned.

[51] Int. Cl.$^5$ .......................... A61F 2/06; A61F 2/02; A61F 2/04
[52] U.S. Cl. ........................ 623/1; 623/11; 623/12; 600/36
[58] Field of Search ............... 623/1, 11, 12; 606/190, 606/191, 192, 193, 194, 195, 196, 197, 198, 199, 200; 600/36

[56] References Cited

U.S. PATENT DOCUMENTS

| | | | |
|---|---|---|---|
| 4,416,028 | 11/1983 | Erickson et al. | 623/1 |
| 4,713,075 | 12/1987 | Kurland | 623/13 |
| 4,960,423 | 10/1990 | Smith | 623/1 |
| 5,024,671 | 6/1991 | Tu et al. | 623/12 X |
| 5,035,708 | 7/1991 | Alchas et al. | 623/1 |
| 5,061,281 | 10/1991 | Mares et al. | 623/11 |

FOREIGN PATENT DOCUMENTS

| | | | |
|---|---|---|---|
| 3323430 | 1/1985 | Germany | 623/12 |
| 2172960 | 7/1987 | Japan | 623/1 |
| 0904693 | 2/1982 | U.S.S.R. | 623/1 |
| 8500511 | 2/1985 | WIPO | 623/13 |
| WO912498 | 3/1991 | WIPO | |

*Primary Examiner*—Randall L. Green
*Assistant Examiner*—Dinh X. Nguyen
*Attorney, Agent, or Firm*—Lahive & Cockfield

[57] ABSTRACT

A polylumenal implantable device comprises a body defining a plurality of capillary lumina. The prosthetic device is suitable for implantation in a patient as an arterial or venous bypass graft or shunt, or intra-organ implant as well as other purposes. The improved prosthetic device has increased surface area and preferably a three-dimensional porosity for encouraging the harboring of, for example, endothelial cells, as well as for receiving organized deposition of material such as genetically enhanced cell types. A method for providing a bioactive material to a patient includes the steps of providing a polyluminal implantable organ comprising an implantable body defining a plurality of capillary lumina, treating the interior surfaces of the lumina with a bioactive material or plasma polymerization, and implanting the prosthetic device in the patient so that bodily fluids of the patient come into contact with the treated interior surfaces.

32 Claims, 2 Drawing Sheets

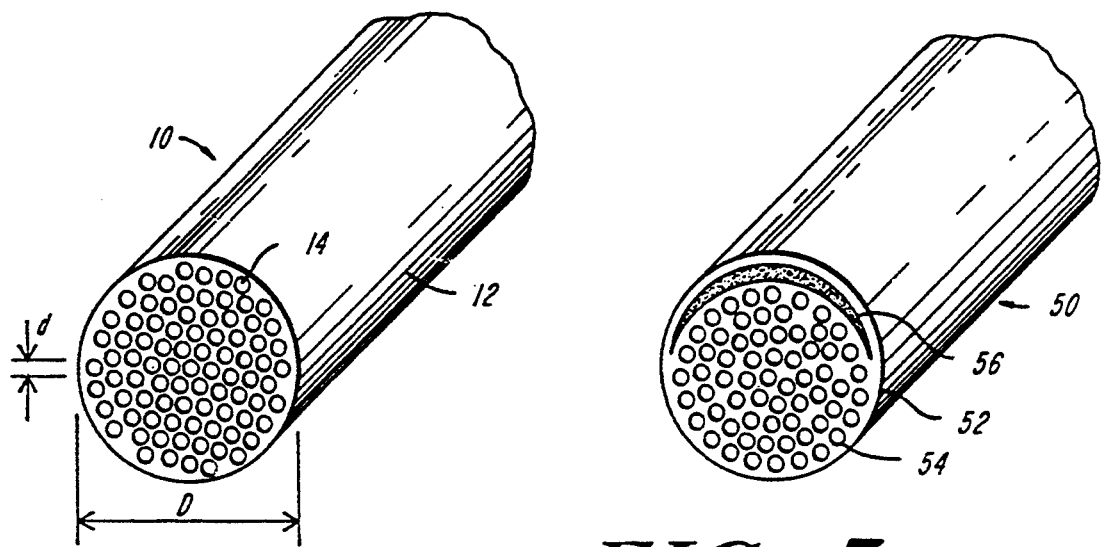
FIG. 1
FIG. 5
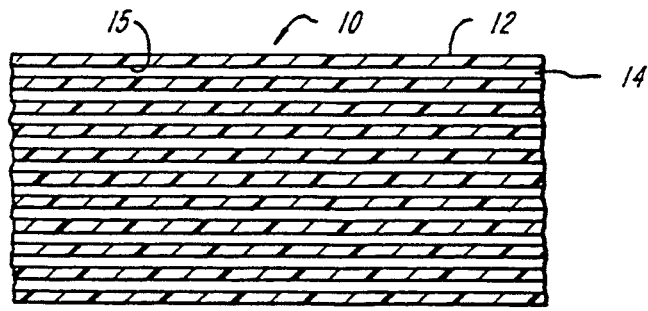
FIG. 2
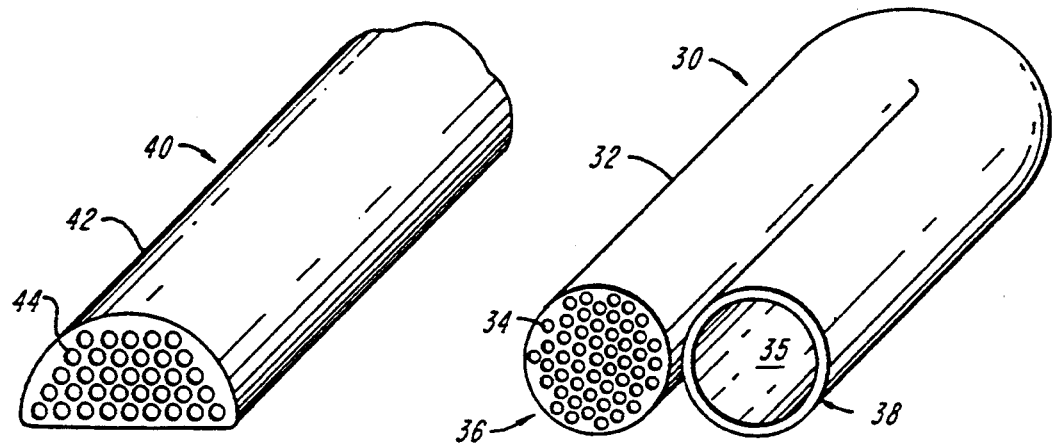
FIG. 4
FIG. 3

POLYUMENAL IMPLANTABLE ORGAN

This application is a continuation of application Ser. No. 760,717, filed Sep. 16, 1991, abandoned.

BACKGROUND OF THE INVENTION

One type of implantable device is a synthetic vascular graft such as is commonly used to replace damaged or dysfunctional arterial or venous pathways, for example at the site of an aneurysm or occlusion. Bypass grafts are often used to divert blood flow around damaged regions to restore blood flow. Another use of vascular prostheses is for creating a bypass shunt between an artery and vein, specifically for multiple needle access, such as is required for hemodialysis treatments. Following multiple percutaneous invasions into a vein, the vein may either collapse along the puncture track or become aneurysmal, leaky or fill with clot, causing significant risk of pulmonary embolization. Vascular prostheses have been used for many years as an alternative to patients' own veins for vascular access during hemodialysis.

Materials research has lead to the development of some acceptable synthetic materials for use in the vascular prosthesis field. An example of one such material is polytetrafluoroethylene (PTFE), a microporous organic material which can be stretched to a specific length and expanded to a specific thickness. When thus stretched, or expanded, PTFE forms a network of interrelated nodes and fibrils. The diameters of the fibrils and internodal distances vary depending upon the conditions and rate at which the PTFE is stretched and/or expanded. Typical stretched and/or expanded PTFE articles have an internodal distance ranging from approximately twenty to approximately thirty microns.

An advantage of stretched and/or expanded PTFE is that the diameters of the fibrils can be made much smaller than the diameters of fibrils of knitted or woven fabrics which have previously been used for vascular prostheses. Moreover, due to the ability to control the pore diameter and porosity of PTFE tubing used, for example, for vascular prostheses, it is possible to decrease the occurrence of thrombosis associated therewith.

Various other synthetic materials, in addition to PTFE, have been used for vascular grafts, including Dacron® brand and other synthetic polyester fibers, mandrel spun polyurethane, and silicon elastomer fibers. Additionally, vascular grafts have been formed using autologous saphenous vein, modified bovine carotid xenograft, and modified human umbilical vein. None, however, has overcome the problems associated with early failure of the graft following implantation.

Other problems associated with vascular grafts formed of known materials and configurations are that their biocompatibility, non-thrombogenic potential, cell harboring, and seeding properties are limited. Specifically, for example, intimal hyperplasia, which is a naturally occurring phenomenon characterized by progressive cellular closure of a blood vessel lumen, threatens the patency of almost all known vascular graft material. Even when surgically repaired or exposed to less intensive manipulative techniques such as balloon dilation, mechanical dilation, laser ablation or mechanical dissection by anthrectomy, intimal hyperplasia is the primary cause of stenosis of all implantable vascular grafts and restenosis of natural arteries following repair of diseased blood vessels.

One cause of intimal hyperplasia is the proliferation of smooth muscle cells into the lumen of the graft. Other causes include injury to the venous system and/or arterial circulation network, caused by trauma, disease, or systemic factors such as hypercholesterolemia.

While intimal hyperplasia is known to cause significant luminal obstruction of vascular grafts, the detailed cellular mechanisms leading to smooth muscle cell proliferation are not completely understood. It is believed, however, that growth factors such as platelet derived growth factor (PDGF) initiate a number of intracellular events, called "regulatory signals." These signals include the activation of protein kinase C. Additionally, different growth-stimulating factors are thought to initiate different signals. These different signals lead to a set of common pathways which stimulate DNA synthesis. Such pathways are called "obligatory events." It is not clear which of these obligatory events, though, are responsible for intimal hyperplasia.

Also, luminal blood vessel injury, whether microcapillary (0.5 mm or less diameter) or aortic (up to 30 mm diameter), induced by trauma, such as mechanical stress, or progressive disease states such as arteriosclerosis or mechanical hemodynamic stress, causes activation of platelets, injury and necrosis of smooth muscle and endothelial cells, and resultant leukocyte infiltration. These events result in the production and release of factors that stimulate smooth muscle cell migration and proliferation from adjacent tissue, subsequently leading to intimal hyperplasia. As stated, such growth, when induced by trauma or progressive disease, without pharmacologic intervention, causes stenotic closure and failure of most autogenous organ transplantations such as coronary artery bypass grafting and synthetic implantable vascular graft devices.

Known treatments of intimal hyperplasia involve the administration of various drugs that inhibit muscle cell proliferation. For example, somatostatin inhibits tumor cell growth. Angiopeptin, a synthetic peptide analog of somatostatin, reduces myointimal proliferation. Trapidil, an antianginal agent possessing vasodilatory and antiplatelet properties, and Terbinafine, an antifungal agent, both are effective antiproliferative agents. Colchicine, a drug which possesses antimitotic and antisecretory properties, also is effective in reducing myointimal thickening.

Besides antiproliferative agents, drugs that inhibit the synthesis and secretion of extracellular matrix are also useful, since a large proportion of the restenotic tissue is composed of extracellular matrix. Because smooth muscle cell migration is an essential step in intimal proliferation, agents that inhibit SMC migration ultimately inhibit proliferation.

Other techniques have been developed, for improving the patency of implantable devices. One such process is glow discharge polymerization as taught by U. S. Pat. No. 4,632,842 to Karwoski et al. Karwoski teaches coating, by the use of glow discharge conducted in a tubular reaction vessel, the surface of an elongate organic substrate with substantially uniform, very low surface-energy coating. Still, even with the Karwoski teaching, the proliferation of smooth muscle cells into known prosthetic vascular grafts is not controlled or reduced sufficiently to prevent intimal hyperplasia.

Another problem associated with known prosthetic devices arises in connection with the use of such devices as a means for drug delivery. That is, while it is known that various prostheses can be coated with bioactive and pharmaceutic agents for blood contact, the limited blood contact surface area within the single lumen of known prostheses used for this purpose limits the amount of agent that can be effectively distributed into the flow through body fluid. Additionally, the high ratio of blood flow-through to contact surface area results in a high level of wash-off.

SUMMARY OF THE INVENTION

This invention pertains to an implantable prosthetic device for sustained release of a bioactive material into a fluid flow pathway of a patient. The device comprises a body formed of material suitable for implantation which defines a multiplicity of capillary lumina. The body is adapted for connection to the patient's fluid flow pathway to establish fluid flow through the capillary lumina. The lumina are separated by walls, formed by the body, which are sufficiently permeable to allow transluminal permeation of a bioactive material.

The inventive prosthetic device acts as an artificial organ for accommodating various types of fluid flow. For example, the device can be grafted to a patient's vascular system whereby it will act as an artificial blood vessel for transporting blood flow. The device can also be implanted in a patient, however, to transport flow of other types of bodily fluids. By seeding selected lumina of the device with a bioactive material, such as a therapeutic agent, diagnostic agent, or cultured cell type, for contact with the body fluid, such as blood, the fluid can be treated by its passing through the device. For example, by seeding selected lumina with liver cells and connecting the device with the patient's vascular system, an artificial organ for detoxifying blood is formed.

While in a preferred embodiment the lumina defined by the implantable body are substantially equal in diameter, in some applications the lumina may be of unequal diameter. In any case, the lumina will typically be of an internal diameter between approximately 0.5 mm and 6 mm, depending upon the outer diameter of the body and the anatomical application for which the device is being used.

In a particularly advantageous embodiment of the invention, interior surfaces of the lumina are coated with a bioactive agent which can be released into biological fluid flowing through the lumina.

Recently published evidence indicating that cellular activities are controlled by receptors, "molecular switches" on the membrane surface of cells, suggests that bioactive and pharmaceutical drug interactions, whether initiators or inhibitors, can be utilized to improve implantable organ and autogenous organ transplant performance. These receptors control cellular activities by binding with highly specific substances referred to as "ligands." Like the action of a key in a lock, ligands fit into receptors and, if the fit is precise, turn on or off certain cellular processes. Some ligands act as antagonists to inhibit cellular activities by blocking a receptor. Research has shown that many aspects of cardiovascular disease are controlled by specific cell surface receptors.

It is a feature of the invention, therefore, to provide site specific drug delivery to an affected area for either initiator or inhibitor drug treatment. This is facilitated by the implantable organ which allows blood or other body fluid to flow through it and to contact or pick up an agent such as, for example, a specific protein, drug, enzyme, or antibody being secreted by the multiple luminal flow surfaces of the implantable device.

Depending upon the site of the implant, each anatomical application may require totally different pharmacological agents as well as different rates of diffusion across the blood contacting barrier from site to site. Each anatomical site may require replacement from time to time, depending upon the drug or combination of drugs required. Regardless of the application or biological activity, however, the basic principle of passive drug diffusion across a luminal microporous membrane into a flowing body fluid, remains the same.

Since various combinations of antiproliferative agents are known to be effective inhibitors of intimal hyperplasia, it is another feature of the invention to provide effective site-specific delivery of these antiproliferative agents. This feature helps to prevent stenosis and restenosis of the implantable device of the invention.

Typically, the implantable device of the invention is cylindrically shaped. It can, however, be adapted to other profiles for given applications. For example, the body can be extruded to be D-shaped with a flat or flattened surface, so as to have a low profile. This may be desirable where the implantable device is to be implanted just under a patient's skin and needs, therefore, to be unobtrusive.

Various extrudable materials are suitable for forming the implantable body of the invention. In particular, expanded polytetrafluoroethylene (ePTFE) has been found to be well suited for the present invention. When using PTFE for this purpose, as described in greater detail herein below, a paste of the material is extruded in the basic form of the implantable device which is then expanded at a specified rate to create an interrelated network of nodes and fibrils.

The invention also features a method for providing a bioactive material to a patient comprising the steps of treating the interior surfaces of the lumina of an implantable device with a bioactive material as described above and implanting the device in a patient so that the patient's bodily fluids pass through the lumina and come into contact with the interior surfaces. Typically, the device is implanted so that it is in fluid communication with the patient's arterial or venous system. Additionally the device can be used to create an arterial-venous shunt for hemodialysis or vascular access. Other methods of implantation, such as intra-organ implantation, can be utilized as well.

Various methods that are generally known in the art can be used for treating the interior surfaces of the lumina with bioactive materials. In one embodiment such treatment may consist of entirely filling selected lumina with a biologically active material or pharmaceutical matrix for diffusion through the walls and into the adjacent lumina which contain body fluid, such as blood. In another embodiment, the interior surfaces may be coated with such a material, or may be coated or seeded with cells that are to incubate and culture within specific lumina or the prosthesis. This may involve first coating or modifying the surface with glycoproteins such as fibrinectin or pretreatment with plasma polymerization application, followed by seeding of the surface with a desired cell type, such as autogenous or genetically enhanced endothelial cells, islet of lagerhans pancreatic cells, or those of a particular organ.

In another example of use of the invention, autogenously derived cultured cells and genetically engineered cell complexes which produce and secrete organ specific proteins, enzymes, initiators, or inhibitors can be seeded in the lumina for introduction to a body fluid flow pathway. For example, cultured cells which incubate within the lumina can be injected into the lumina prior to implantation, to produce a desired pharmaceutical agent for diffusion across the luminal fluid contacting surface. Also, cultured cells to grow through the microporous luminal membrane and actually line blood contacting surface for direct cell to blood contact and resultant receptor/inhibitor stimulation, and/or secretion.

These and other features of the invention will be more fully appreciated by reference to the attached specification which is to be read in conjunction with the attached drawings in which the same reference numerals refer to the same elements throughout the several views.

BRIEF DESCRIPTION OF THE DRAWINGS

FIG. 1 is a perspective view of one embodiment of a polylumenal prosthetic device constructed in accordance with the teachings of the present invention;

FIG. 2 is a cross section view taking along line 2—2 of FIG. 1;

FIG. 3 is a perspective view of another embodiment of the prosthetic device of the present invention;

FIG. 4 is a perspective view of still another embodiment of the prosthetic device of the present invention;

FIG. 5 is a perspective view of yet another embodiment of the prosthetic device of the present invention.

DETAILED DESCRIPTION

Figure 6A:
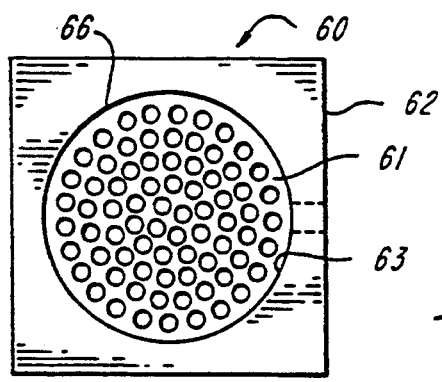
FIGS. 6A and 6B are schematic views of a die suitable for extruding a polylumenal prosthetic device constructed in accordance with the teachings of the present invention.

In its broadest aspect the invention features an implantable device formed of a microporous body material which defines a multiplicity of coextruded, molded, or otherwise formed capillary lumina and an outer boundary or wall which circumscribes the lumina. In FIG. 1, an embodiment of the invention is shown wherein a polyluminal device 10 is formed of an implantable body 12. The body 12 defines a multiplicity of lumina 14 for transporting fluid flow. The outer circumference of the implantable device 10 is indicated as D while the diameter of a typical capillary lumen is indicated as d. Specific values of these characteristics are discussed in greater detail herein below. As described in greater detail below, the device 10 can be formed by any number of paste forming methods such as by, for example, extrusion.

FIG. 2 is a cross-sectional view of the implantable organ 10 and shows that in this embodiment of the invention the capillary lumina 14 extend the entire length of the device 10 is channeled through the lumina 14 for its entire course. In another embodiment of the invention, however, the lumina 14 do not extend along the entire length of the device 10.

In either case, however, the device 10 has the further property that its structural material has a sufficiently microporous to allow communication of cells and extracellular fluid in a direction transverse to the capillary axes. This communication allows cell processes to penetrate the structural material. It also allows the selective trans-lumenal passage of extracellular matter, such as marker chemicals governing cell or organ growth patterns.

In addition to providing a more delicate ultrastructure to encourage cell motility, one advantage afforded by the capillary lumina structure of the device 10 is realized, for example, when the device 10 is utilized as a vascular graft. Increased blood contact surface area 15 makes the device 10 more conducive than known implantable organs having only a single luminal surface to harboring endothelial cells. This is as a result of the device 10 providing reduced shear pressure on fluid flowing through the lumina 14.

Other advantages of the multiple capillary lumina structure include improved cellular distribution for blood contact and more surface area for supporting the growth of more specialized cell types. Furthermore, the porosity of the body 12 allows perfusion of necessary bioactive and pharmaceutical agents for cell growth, and cell to cell membrane contact necessary for cell metabolism, replication, and subsequent replacement after cell death. Generally, endothelial cell growth is stimulated by several factors, including the binding or adhesive action of glycoproteins such as fibrinectin. When the implantable device is precoated with a glycoprotein, therefore, there is an improvement in adhesion of seeded cells, increasing retention and migration of cells during cell growth.

Another advantage of the capillary lumina structure of the device 10 is that relatively small flow channels provide a more desirable shear blood flow characteristic than do large flow channels. As a result, the survival of naturally occurring endothelial cells is enhanced which stays the proliferation of smooth muscle cells into the flow channels. This is significant because, as discussed above, smooth muscle cell proliferation has been clinically identified as a common obstacle inhibiting long term or extended patency of single lumen vascular grafts. By inhibiting the proliferation of smooth muscle cells by creating a more natural flow environment through the capillary lumina 14, therefore, the device 10 is capable of remaining patent for an extended period of time, longer than known single lumen grafts constructed of the same structural material.

For a lumen to accommodate the flow of blood cells, its diameter must be at least approximately 0.5 mm. So, to ensure blood flow while simultaneously providing desirable shear characteristics, the diameter d of the device 10 when used as a vascular graft is preferably between 0.5 mm and 6 mm, depending on the anatomical and fluid flow requirements. As a result, as used herein, the term capillary, when referring to the lumina 14 of the device 10, generally means lumina having an internal diameter ratio of at least 0.5 mm I.D. for O.D.'s of 3 mm, 1 mm I.D. for O.D.'s of 6 mm, and 5 mm to 6 mm I.D. for O.D.'s of 30 mm. It can be seen, therefore, that the ratio of lumina inner diameter to the overall outer diameter of the device is typically approximately one to six.

In addition to encouraging improved harboring of naturally created and/or autogenously cultured and seeded endothelial cells, the increased surface area 15 provides more area for deposition and growth of naturally occurring or seeded genetically enhanced cell types in addition to providing more surface area for bioactive and pharmaceutical fluid and cell interface or contact.

For example, the following chart lists typical pharmaceutical agents appropriate for either coating on the walls of the lumina 14 of the device 10 or filling selected lumina. A combination of the two techniques may be desirable as well. Also included in the chart is the desired effect achieved by the listed pharmaceutical.

| Drug Class | Biological Activity |
| --- | --- |
| Steroids | Antiinflammatory, Antiproliferatory for SMC |
| Ibuprofen (non-steroid) | Antiinflammatory |
| Trombin Inhibitors | Reduce Acute Platelet Thrombosus |
| -Haparin | Antiproliferatory for SMC |
| -Hirudin | Thrombin Inhibitio |
| Citrates | Anticoagulant |
| Antibiotics | Infection Protection, Prevention, Reduction |
| Glycoproteins/ Fibronectin | Promotes specific cell attachment to foreign material |
| Angiotensin | Enzyme Inhibitor |
| Cyclosporin | Immuno Suppressive Activity |
| γ-Interferon | Immuno Suppressive Activity |
| Angiopeptin | Antiproliferatoy for SMC |
| Trapidil | Antianginal Agent, Vasodilator, Antiplatelet Activity |
| Colchicine | Antimitotic, Antisecretory Property |
| Dipiridymole | Antiplatelet |
| Salicylic Acid | Antiplatelet, Inhibits Thromboxane $A_2$ Production ($TXA_2$) |
| $PGI_2$ (Protaglandin $I_2$) | Antiaggregation and Vasodilation |
| TRA (Thromboxane Receptor Antagonists) | Blocks $TXA_2$ Receptors without inhibiting PGI2 production |
| Nitric Oxide | Relaxes smooth muscle cells, potent antiplatelet aggregating substance |
| Five Types of Plasminogen Activators 1. Steptokinase 2. Acylated Steptokinase Plasminogen Activator Complexes(APSAC) 3. Urokinase 4. Single-Chain Urokinase Plasminogen Activator (scu-PA) 5. Tissue Plasminogen (t-PA) | Thrombolytic agents - potent clot dissolvers |
| Combinations of Tissue Plasminogen Activator and Thrombin Inhibitors (i.e., T-PA and Hirudin) | Treatment of acute vascular graft thrombosis, or prevention of same |
| Lovastatin | Antiproliferatory for SMC |
| Cytotoxic Agents | Various, tumor specific chemotherapy agents |
| Insulin | For treatment of diabetes mellitus |
| Beta Blockers | For treatment of arrhythmia |

In FIG. 3 there is shown an embodiment of the invention wherein an implantable device 30 is formed of an implantable body 32 which defines a plurality of capillary lumina 34. In accordance with the device 30, however, one end 36 defines the capillary lumina 34 while another end 38 defines only a single lumen 35. This embodiment of the invention is well suited for artery to vein grafting wherein the end 36 defining the lumina 34 is connected to an artery of a patient while the end 38 defining only single lumen 35 is connected to a vein of the patient. As a result, the ability of the capillary lumina defining end 36 to prevent arterial steal syndrome is exploited.

Arterial steal occurs when an equivalent size lumen device is bypassed from an originating artery to a lower pressure vein. Under such circumstances, arterial flow can preferentially flow through the bypass device in the vein, thereby reducing flow pressure to the distal destination of the originating artery. Hence the term arterial steal, which is an undesirable effect when creating such arterio-bypass shunts. When a multiluminal device is used for such arterio-venous bypass or shunting, the increased flow resistance of the smaller lumens do not allow unrestricted flow, therefore, preventing arterial steal from occurring.

Another embodiment of the invention is shown in FIG. 4 wherein a implantable device 40 incorporates a capillary lumina structure 44 circumscribed by an outer wall or boundary 42 having a D-shaped profile. This broader, flatter structure provides better needle access and is less conspicuous in situations in which the device is implanted close to the surface of a patient's skin. Note also that the infra-structure of the device 40 provided by the walls of the lumina 44 provides improved internal strength for confronting the deleterious effects of repeated needle access. That is, the implantable organ of the invention will withstand more needle punctures without aneurysm formation blowout, than well known single lumen vascular grafts which succumb to such undesirable events.

Still another embodiment of the invention is shown in FIG. 5 which shows a prosthetic device 50 that includes, in addition to a plurality of capillary lumina 54, a larger lumen 56 located just under the surface of the outer wall 52. This larger lumen 56 is suitable for containing, for example, either a self sealing elastomeric material for providing the device 50 with self sealing capability or a bioactive material such as a pharmaceutical agent. The larger lumen 56 enhances the device's ability to deliver bioactive material to a patient's blood stream through the microporous structure, directly into the blood or body fluids flowing through the multiple capillary lumens.

The prosthesis of the invention can be manufactured from any suitable biocompatible material, such as PTFE, Dacron ®, or other synthetic polyester, or mandril spun polyurethane or silicone elastomer microfibers that can be arranged to form a microporous structure. Hybrid constructions of these same materials are suitable as well. Also, copolymeric materials such as described in U.S. Pat. Nos. 4,187,390 and 4,973,609 can be utilized. These are materials made up of more than one type of monomer and have advantages, in various applications, described in the cited patents. The structures may be extruded, form molded, mandrel spun fiber, or woven using techniques well known in the field. In a preferred embodiment, described in further detail below, the implantable device is manufactured from stretched and/or expanded PTFE tubing by rapidly stretching highly crystalline unsintered polytetrafluoroethylene in one or more planes of axis.

The tube structures of the invention may be made by extrusion of tetrafluoroethylene resins, such as polytetrafluoroethylene (PTFE) or blends of various types of resins. Paste forming and extrusion of materials such as PTFE and blends of various types of PTFE, including the coextrusion of one or more reference lines, are well-known in the art. Generally, the steps in paste-forming include mixing the resin with a lubricant, such as odorless mineral spirits, and then forming the resin by extrusion into shaped articles. The lubricant is removed from the extruded shape by drying following which the product is sintered by its being heated above its crystalline melting point. In the case of PTFE, this is approximately 327° C. The sintered unexpanded product thus becomes a relatively impermeable product. However, to achieve a degree of permeability, the implantable organ of the invention may be formed from an unsintered resin.

As described in detail in U.S. Pat. No. 3,953,566 (Gore, Apr. 26, 1976), paste-formed, dried, unsintered shapes can be further treated by expanding and/or stretching them in one or more directions under certain conditions so that they become microporous yet retain their strength. Such stretching and expansion with increased strength occurs with certain preferred tetrafluoroethylene resins, e.g., PTFE. The porosity of the material is affected by the temperature and rate at which it is stretched and/or expanded. A method for manufacturing microporous PTFE tubing appropriate for use in the present invention is described in detail, in the above referenced Gore patent as well as U.S. Pat. No. 4,973,609 (Browne, Nov. 27, 1990), the teachings of both of which are hereby incorporated herein by reference.

Stretched and expanded PTFE is characterized by a microstructure of large nodes interconnected by fibrils. The space between the nodes, internodal distance, and the number of fibrils is controlled by changing the temperature and rate of expansion of the PTFE to produce structures having predetermined porosity and flex qualities. Internodal distances of from smaller than approximately 0.5 microns to as large as approximately 60 microns are suitable for use with the present invention.

Products which are expanded at high temperatures and high rates have a more homogeneous structure, i.e., they have smaller, more closely spaced nodes, which nodes are interconnected with a greater number of fibrils. While the resulting structure is stronger than products expanded at lower temperatures and rates, the porosity is also reduced. Thus, by controlling the two factors, it is possible to construct a series of tube structures having a range of porosity within a desirable range of strength.

It has been noted that when tube structures, manufactured as described above, are heated to above the lowest crystalline melting point of the PTFE, disorder begins to occur in the geometric order of the crystallites and the crystallinity decreases. This is accompanied by a concomitant increase in the amorphous content of the polymer. So formed amorphous regions within the crystalline structure greatly inhibit slippage along the crystalline axis of the crystallite and lock fibrils an crystallites so that they resist slippage under stress. Heat treatment may be considered to be, therefore, an amorphous locking process, the important aspect of which is an increase in the amorphous content of the treated structure. In fact, heat treatment above 327° C. has been found to cause a two-fold increase in the strength of PTFE tubular structures.

Since the upper melting range of PTFE is approximately 345° C., heat treatment above this temperature is even more effective. Similar results can be achieved at lower temperatures if exposure time is accordingly increased. In one embodiment of the invention, the optimum heat treating temperature is in the range of from about 350° C. to about 370° C., with heating periods in the range of from about 5 seconds to about 1 hour. Other factors upon which the strength of the polymer matrix is dependent upon are the strength of the extruded material before expansion, the degree of crystallinity of the polymer, the rate and temperature at which the expansion is performed, and amorphous locking.

In another aspect of the invention, the tube structures can be formed using other paste-forming operations known to those skilled in the art, such as, for example, any of the available molding processes. Paste-forming resins other than PTFE may also be used which are generally formable into such tube structures, and which may result in relatively fluid impermeable structures. Due to the physiological properties of the arteriovascular system, it is important for the tube structures to be gas permeable, or selectively gas permeable, to permit oxygen-carbon dioxide exchange. However, even gas impermeable tube structures may be useful as vascular grafts in certain AV regions.

Figure 6B:
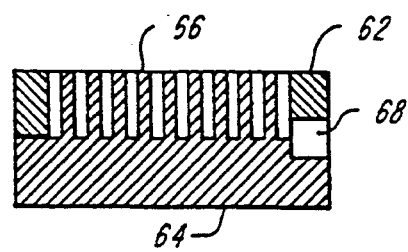

As stated, in the preferred embodiment the tube structures of the present invention are formed by extrusion and expansion of PTFE. Extrusion is performed using dies of predetermined shape which is determined by considerations known in the art. FIGS. 6A and 6B schematically show an exemplary die 50, corresponding to the illustrated prosthesis of FIG. 1. The die may be manufactured from materials available and well known in the art.

Generally, and as illustrated, the die 60 consists of an upper plate 62 and a lower plate 64. The upper plate 62 defines a circular edge 63 corresponding to the outer diameter of the tubular structure 10. The lower plate 64 defines a plurality of finger-like projections 66 corresponding to the lumina 14 of the prosthetic device 10. The specific dimensions of the projections 66 and their spacing from one another depend upon the specific desired prosthesis configuration. This spacing will dictate, for example, the thickness of the common side walls 15. As best shown in cross-section in FIG. 6B, the die 60 typically includes a channel 68 for introduction of PTFE paste, or the like, under pressure for extrusion. In practice, the extruded material is supported or carried as it exits the die, so that tensile or compressive forces are controlled and the capillary passages remain open. As discussed above, the material may then be subjected to heat or other treatment for sintering, solvent removal or the like.

After the PTFE resin is formed, such as by extrusion as discussed above, it is stretched and/or expanded and then sintered while being held in the stretched and/or expanded state. Stretching refers to elongation of formed resin while expansion refers to enlargement of the formed resin perpendicularly to its longitudinal axis. The rate of stretching and the stretch ratio affect the porosity of the finished product in a predictable manner allowing a prosthetic device to be produced having a specified porosity. The rate of stretching refers to the percentage of elongation per second that the resin is stretched while the stretch ratio refers to the relationship between the final length of the stretched resin and the initial length of the stretched resin. For example, stretching an extruded PTFE tube at a stretch ratio of two to one and a stretch rate of sixty results in a porosity of approximately forty. This porosity is unitless and is determined as set forth on page eighty-four of the American Society For Testing of Materials' Special Technical Publication Number 898. So, for example, based on stretch ratios ranging from two to one, to six to one, a stretch rate of sixty percent per second yields a porosity of between approximately forty and approximately ninety, a stretch rate of one hundred and forty percent per second yields a porosity of between approximately sixty and approximately eighty-five, and a stretch rate of nine hundred percent per second yields a porosity of between approximately sixty-five and approximately eighty-five.

In addition to the porosity, the geometry of the node and fibril network of stretched PTFE can be controlled during stretching. In the case of uniaxial stretching, which is along the direction of extrusion, the nodes are elongated causing the longer axis of each node to be oriented perpendicularly to the direction of stretch. Accordingly, the fibrils are oriented parallel to the direction of stretch. By axial stretching, which includes expanding the material in the radial direction in addition to uniaxial stretching, can be utilized to produce a prosthetic device having a composite porosity. As in linear stretching, the rate and ratio of stretching and expansion affects the resulting porosity of the prosthetic device.

The invention contemplates that in various embodiments the prosthesis may serve not only as a flow structure, but as a matrix and support upon which cellular matter is grown while blood circulates therethrough. For these embodiments, the device may be prepared and seeded with culturable cells, e.g., marrow or organ cells, or endothelial cells which have been genetically modified to produce a desired bioactive material, and may then be implanted in an organ or connected to the AV system. Examples of typical cell types useful for this purpose and their corresponding biologic activities follow.

| Cell Type | Biologic Ativity |
| --- | --- |
| EC (Endothelial Cells) | Endothelial cells line the blood contacting surface of all organs of the body and product many initiators and inhibitors involved in wound healing, thrombosis, thrombolysis and blood vessel regeneration and cell growth, for direct perfusion into blood stream |
| Islets of Langerhans | Islet Cells produce insulin on demand, based on complex receptor blood sugar chemistry. |
| Pancreatic Cells | directly into the blood stream by the islet cells |

For these embodiments, the spacing between capillaries is preferably small, and may approach membrane thickness in places, to allow communication by direct physical processes or by fluid mediators between cells growing in different capillaries. The body of the prosthesis thus provides a first plurality of capillary channels for direct physical flow of flood for supplying nutrients to living tissue growing on the capillary walls, and a second set of transverse pores or openings of substantially smaller size for communication between cells, so that they may flourish in a three-dimensional matrix. The relatively open or microporous matrix is expected to allow cellular material to grow into micro structures which are similar to those of the structures in which the parent cells naturally occur, thus providing an effective environment for in vivo culture of specialized cell types. As such, it offers the prospect of providing an effective form of organ replacement or supplemental therapy.

In an another embodiment, specific autogenously derived and genetically engineered growth factors can be inoculated into various lumina for body fluid contact. Such growth factors are specific proteins borne by flood platelets that trigger tissue healing.

| Protein Class | Biologic Activity |
| --- | --- |
| PDGF Protein (Platelet derived growth factor) | Wound healing factor, encourages growth of new blood vessels |
| EGF (Epidermal Growth Factor) | Promotes wound healing, healing of ulcers reduced degradation and faster recovery of transplanted organs |
| bFGF (basic fibroblast growth factor) | Signals subdermal tissue growth, promotes blood vessel growth, bone graft growth |
| TGFb (transforming growth factor Beta) | Promotes wound healing of ulcers caused by varicose veins and diabetic ulcers |
| Erythropietin | Promotes red blood cell growth |
| GCSF (Granulocyte colony Stimulating factor) | Promotes white blood cell growth |
| GMCSF (Granulocyte macrophage colony Stimulating factor) | Promotes white blood cell growth |
| Iamin (Tripeptide) | Attracts and triggers various cell specific growth factors following trauma |
| BGF-1 (Heparin-binding growth factor-1) | Stimulates blood vessel growth |
| CD4 Protein | Controls growth of AIDS virus |

Other alternations to the described embodiments of the invention which will be readily apparent to those skilled in the art are intended to be embraced within the spirit and scope of the invention. That is, the preceding description is intended as illustrative rather than limiting. The invention is to be defined, therefore, not solely by the preceding description, but by reference to the claims that follow.

What is claimed is:

1. An implantable prosthetic device for connection to a fluid flow pathway of a patient, the device comprising an implantable body made of a single biocompatible material and extruded as a single body with microporous interior walls, said extruded single body having a shape to attach to said fluid flow pathway, said single body further having a multiplicity of capillary lumina therein defined by said microporous interior walls and extending substantially parallel to each other along a longitudinal axis of the body for accommodating fluid flow along said axis when attached to said fluid flow pathway.

2. A device as set forth in claim 1 wherein said microporous walls are sufficiently permeable to allow transluminal communication of cells and extra-cellular fluid.

3. A device as set forth in claim 1 wherein said implantable body is of a first diameter and said lumina are of a second diameter, said first diameter being approximately six times greater than said second diameter.

4. A device as set forth in claim 1 wherein all of said multiplicity of capillary lumina are of substantially equal diameter.

5. A device as set forth in claim 1 wherein each of said lumina is defined by an interior surface, said interior surfaces being treated with a bioactive material selected from the group consisting of protein, glycoprotein, and growth factors.

6. A device as set forth in claim 1 wherein said body has a D-shaped cross-section.

7. A device as set forth in claim 1 wherein said implantable body consists of polytetrafluoroethlene.

8. A device as set forth in claim 7 wherein said polytetrafluoroethylene is selected from the group consisting of expanded polytetrafluoroethylene, stretched polytetrafluoroethylene, and expanded and stretched polytetrafluoroethylene.

9. A device as set forth in claim 1 wherein said implantable body consists of a material including copolymers.

10. A device as set forth in claim 1 wherein selected capillary lumina are filled with a bioactive material.

11. A device as set forth in claim 10 wherein said bioactive material is a therapeutic agent.

12. A device as set forth in claim 10 wherein said bioactive material is a diagnostic agent.

13. An implantable prosthetic device for sustained release of a bioactive material into a patient's blood stream, the device comprising an implantable tubular body formed of a single porous biocompatible material and adapted for attachment to a blood vessel of the patient, said implantable body including a body portion extruded as a single segment with a plurality of interior walls defining a multiplicity of capillary lumina extending substantially parallel to a longitudinal axis of the body portion and of a size for accommodating blood flow therethrough, said single segment being porous such that said interior walls are permeable to allow transluminal permeation of a bioactive material.

14. A device as set forth in claim 13 wherein said implantable body is of a first diameter and said lumina are of a second diameter, said first diameter being approximately six times greater than said second diameter.

15. A device as set forth in claim 13 wherein all of said multiplicity of capillary lumina are of substantially equal diameter.

16. A device as set forth in claim 13 wherein each of said lumina is defined by an interior surface, said interior surfaces being treated with a bioactive material selected from the group consisting of protein, glycoprotein, and growth factors.

17. A device as set forth in claim 13 wherein said outer wall is D-shaped.

18. A device as set forth in claim 13 wherein said implantable body consists of polytetrafluoroethylene.

19. A device as set forth in claim 18 wherein said polytetrafluoroethylene is selected from the group consisting of expanded polytetrafluoroethylene, stretched polytetrafluoroethylene, and expanded and stretched polytetrafluoroethylene.

20. A device as set forth in claim 13 wherein selected capillary lumina are filled with said bioactive material.

21. A device as set forth in claim 20 wherein said bioactive material is a therapeutic agent.

22. A device as set forth in claim 20 wherein said bioactive material is a diagnostic agent.

23. A method for providing a bioactive material to a fluid flow pathway of a patient, the method comprising the steps of providing an implantable body formed of a single porous biocompatible material and adapted for attachment to said fluid flow pathway and for accomodating fluid flow therethrough, said implantable body being extruded as a single body with a plurality of interior walls defining a multiplicity of capillary lumina extending substantially parallel to a longitudinal axis of the single body, said lumina being separated by walls sufficiently permeable to allow transluminal permeation of a bioactive material, introducing said bioactive material to selected capillary lumina, and surgically grafting said prosthetic device to the fluid flow pathway in the patient to establish fluid flow along said longitudinal axis through others of said capillary lumina through said implantable body.

24. A method as set forth in claim 23 wherein said introducing step is carried out by prefilling said selected capillary lumina with the bioactive material.

25. A method as set forth in claim 23 wherein said introducing step is carried out by coating the interior surfaces of said selected capillary lumina with the bioactive material.

26. A method as set forth in claim 23 wherein said implanting step is carried out by placing implantable body in fluid communication with the patient's vascular system.

27. A method as set forth in claim 23 wherein said implanting step is carried out by placing the implantable body in fluid communication with an internal organ of the patient.

28. A method as set forth in claim 23 further comprising the step of seeding said selected capillary lumina prior to said introducing step with material to promote both naturally occurring and genetically derived and cultured cell attachment and growth.

29. A method for providing a bioactive material to a patient's blood stream, the method comprising the steps of forming from a mass of porous polytetrafluoroethylene by applying heat and pressure, a single body, said body being extended and having plural interior walls and adapted for attachment to a blood vessel of the patient, said plural interior walls of the single body defining a multiplicity of capillary lumina extending substantially parallel to a longitudinal axis of the body and adapted for accommodating blood flow therethrough, said interior walls formed of said porous polytetrafluoroethylene being permeable to allow transluminal permeation of a bioactive material, introducing said bioactive material to selected ones of said capillary lumina, and surgically grafting said prosthetic device to the blood vessel to establish blood flow through at least some of said capillary lumina.

30. A method as set forth in claim 29 wherein said introducing step is carried out by prefilling said selected capillary lumina with the bioactive material.

31. A method as set forth in claim 29 wherein said introducing step is carried out by coating the interior surfaces of said capillary lumina with the bioactive material.

32. A method as set forth in claim 29 wherein said implanting step is carried out by placing implantable body in fluid communication with the patient's vascular system.

* * * * *